United States Patent
Zhou

(10) Patent No.: US 9,052,310 B2
(45) Date of Patent: Jun. 9, 2015

(54) SUBSTRATE IMPRINTED UNIVERSAL SENSORS AND SENSORS HAVING NANO-TUNNELING EFFECT

(76) Inventor: Yanxiu Zhou, Phoenix, AZ (US)

(*) Notice: Subject to any disclaimer, the term of this patent is extended or adjusted under 35 U.S.C. 154(b) by 609 days.

(21) Appl. No.: 12/700,927

(22) Filed: Feb. 5, 2010

(65) Prior Publication Data

US 2010/0203623 A1  Aug. 12, 2010

Related U.S. Application Data

(60) Provisional application No. 61/209,652, filed on Mar. 9, 2009, provisional application No. 61/207,372, filed on Feb. 11, 2009.

(51) Int. Cl.
*G01N 33/543* (2006.01)
*B01J 20/30* (2006.01)

(52) U.S. Cl.
CPC ....... *G01N 33/54373* (2013.01); *B01J 20/3057* (2013.01)

(58) Field of Classification Search
CPC ................ G01N 33/54373; B01J 20/3057
See application file for complete search history.

(56) References Cited

U.S. PATENT DOCUMENTS

| | | | |
|---|---|---|---|
| 7,393,909 B2 | 7/2008 | Sellergren et al. | |
| 2002/0001821 A1* | 1/2002 | Mosbach et al. | 435/35 |
| 2004/0058380 A1 | 3/2004 | Levon et al. | |
| 2007/0281366 A1* | 12/2007 | Shimizu et al. | 436/501 |
| 2008/0071003 A1* | 3/2008 | Sellergren et al. | 522/57 |
| 2008/0179191 A1 | 7/2008 | Zhou et al. | |
| 2009/0087549 A1 | 4/2009 | Zhou et al. | |

FOREIGN PATENT DOCUMENTS

WO  2005/059507 A2  6/2005

OTHER PUBLICATIONS

Levi et al. Optical Detection of Chloramphenicol Using Molecularly Imprinted Polymers. Analytical Chemistry, 1997, vol. 69, No. 11. p. 2017-2021.*
Yanxiu Zhou et al., Potentiometric Sensing of Chemical Warfare Agents: Surface Imprinted Polymer Integrated with an Indium Tin Oxide Electrode, Anal. Chem. 2004, 76, 2689-2693.
Yanxiu Zhou et al., Potentiometric Sensing of Chiral Amino Acids, Chem. Mater. 2003, 15, 2774-2779.
(Continued)

*Primary Examiner* — Melanie Y Brown
(74) *Attorney, Agent, or Firm* — Zeman-Mullen & Ford, LLP

(57) ABSTRACT

A universal sensor fabrication approach, molecular substrate imprinting technique, which utilizes the interaction between molecular building blocks and the surface of a transducer to develop specific molecular recognition cavities has been established. Integration of molecular recognition cavities with the surface of a nanoscale transducer will result in a nano-tunneling effect that takes place which will provide a sensor or a device that exhibits new properties not already exhibited by either the molecular recognition cavities on a bulk transducer or the nanotransducer material. One of the new properties of this nano-tunneling effect is that a universal potentiometric molecular sensor can be fabricated and used to detect any compounds, whether they are ions or molecules, with enhanced selectivity, sensitivity, and stability when molecular recognition cavities or elements are integrated on the surface of a nanoscale transducer.

9 Claims, 7 Drawing Sheets

(56) References Cited

OTHER PUBLICATIONS

Yanxiu Zhou et al., Potentiometric sensor for dipicolinic acid, Biosensors and Bioelectronics 20 (2005) 1851-1855.

Yantian Wang et al., A potentiometric protein sensor built with surface molecular imprinting method, Biosensors and Bioelectronics 24 (2008) 162-166.

Steven C. Zimmerman et al., Synthetic hosts via molecular imprinting—are universal synthetic antibodies realistically possible?, Chem. Commun. 2004, 5-14.

John Anderson, et al., Steady-State and Frequency-Domain Lifetime Measurements of an Activated Molecular Imprinted Polymer Imprinted Dipicolinic Acid, Journal of Fluorescence, vol. 14, No. 3, May 2004.

Yun-Mei, et al., Synthesis and Evaluation of Molecularly Imprinted Polymers Using Acetylsalicylic Acid as Template, Journal of Instrumental Analysis, vol. 26, No. 2, 165-169.

Claudio Baggiani, Adsorption isotherms of a molecular imprinted polymer prepared in the presence of a polymerisable template Indirect evidence of the formation of template clusters in the binding site, Analytica Chimica Acta 504 (2004) 43-52.

Roongnapa Suedee, et al., Development of trichloroacetic acid sensor based on molecularly imprinted polymer membrane for the screening of complex mixture of haloacetic acids in drinking water, Analytica Chimica Acta 504 (2004) 89-100.

C. Baggiani, et al., Binding properties of 2,4,5-trichlorophenoxyacetic acid-imprinted polymers prepared with different molar ratios between template and functional monomer, Talanta 62 (2004) 1029-1034.

Hye-Ryoung Park, et al., Separation of Hydroxybenzoic Acid Isomers Using the Molecular Imprinting Technique, Journal of Applied Polymer Science, vol. 105, 2824-2829 (2007).

Hutting Zhang, et al., Retention behavior of phenoxyacetic herbicides on a molecularly imprinted polymer with phenoxyacetic acid as a dummy template molecule, Bioorganic & Medicinal Chemistry 15 (2007) 6089-6095.

Koji Nemoto, et al., Simple and Effective 3D Recognition of Domoic Acid Using a Molecularly Imprinted Polymer, J. Am. Chem. Soc. 2007, 129, 13626-13632.

Karsten Haupt, et al., Assay System for the Herbicide 2,4-Dichlorophenoxyacetic Acid Using a Molecularly Imprinted Polymer as an Artificial Recognition Element, Anal. Chem. 1998, 70, 628-631.

C. Baggiani, et al., Chromatographic characterization of molecularly imprinted polymers binding the herbicide 2,4,5-trichlorophenoxyacetic acid, Journal of Chromatography A, 883 (2000) 119-126.

Claudio Baggiani, et al., Molecularly imprinted solid-phase extraction sorbent for the clean-up of chlorinated phenoxyacids from aqueous samples, Journal of Chromatography A, 938 (2001) 35-44.

Hui Li, et al., Separation and purification of chlorogenic acid by molecularly imprinted polymer monolithic stationary phase, Journal of Chromatography A, 1098 (2005) 66-74.

K.P. Prathish, et al., Molecularly imprinted polymer-based potentiometric sensor for degradation product of chemical warfare agents Part I. Methylphosphonic acid, Talanta 71 (2007) 1976-1980.

Yu Ping Zhang, et al., Novel preparation of monolithic imprinted columns for electrochomatographic separation by photopolymerization, Chinese Chemical Letters 18 (2007) 734-737.

Yongjian Wang, et al., Specific binding of cholic acid by cross-linked polymers prepared by the hybrid imprinting method, Polymer 48 (2007) 5565-5571.

Hsin-Hung Pan, et al., Synthesis of Molecularly Imprinted Polymer and its Molecular Recognition Properties of N-Acetylneuraminic Acid, E-Journal of Chemistry, vol. 4, No. 4, pp. 611-619, Oct. 2007.

Yun-Mei, et al., Synthesis and Evaluation of Molecularly Imprinted Polymers Using Acetylsalicylic Acid as a Template, Journal of Instrumental Analysis, vol. 26, No. 2, 165-169.

* cited by examiner ated polymer network. Removal of the template molecule from the molecularly imprinted polymer network creates a structure complementary to the template structure allowing its tight and selective uptake.

SUBSTRATE IMPRINTED UNIVERSAL SENSORS AND SENSORS HAVING NANO-TUNNELING EFFECT

CROSS-REFERENCE TO RELATED APPLICATIONS

This application claims the benefit of U.S. Provisional Application No. 61/209,652, filed Mar. 9, 2009, and U.S. Provisional Application No. 61/207,372, filed Feb. 11, 2009, which are both herein incorporated by reference in their entireties.

FIELD OF INVENTION

The present invention relates to substrate imprinted universal molecular sensors and substrate imprinted universal molecular sensors having a nano-tunneling effect as well as methods for making and realizing the same. More particularly, the present invention relates to a sensor that is based on the interaction of molecules, or molecular building blocks, with the surface of transducer substrates to form molecular recognition cavities. These substrate molecular imprinted sensors are universal sensor systems because there is no covalent or non-covalent bonding required between the molecular building blocks and the templates, thus, there is no need to carefully design the interactions between molecule building blocks and template molecules. This molecular substrate imprinting technique can be used to develop sensors for almost any molecule or structure. In addition, if the molecular recognition cavities integrate with the surface of a transducer substrate that is in nanometer scale, a nano-tunneling effect may take place that results in a sensor or other device that exhibits new properties not already exhibited by either the substrate imprinted molecular recognition matrix on a bulk material based transducer or the nanotransducer material itself. The nano-tunneling potentiometric molecular sensors of the present invention can be used to detect any form of compounds, whether in ionic form or not, with enhanced selectivity, sensitivity, and stability.

BACKGROUND OF THE INVENTION

Sensors are devices that measure a physical quantity and convert it to a signal that can be measured by an observer or an instrument. Numerous types of sensors exist including sensors for chemical, biological, mechanical, and optical applications, as well as sensors for combinations of these types of applications. A chemical sensor is a device that furnishes the user with information about its environment. It consists of a physical transducer and a chemically selective layer. The universal molecular sensors made in accordance with the present invention are particularly suited for use as chemical sensors or biosensors. Performance of a sensor is measured by the sensor's selectivity, sensibility, and stability. It is difficult to achieve high levels of all three of these functions at the same time because the sensor's sensing process is actually a molecular recognition process. Molecular recognition includes not only chemical (or biological) recognition, as mentioned above with respect to a chemical sensor, but also physical recognition.

The importance of physical recognition has been realized in the field of sensors by utilizing molecular imprinting to make sensors. Molecular imprinting is a known technique for making synthetic hosts which are the man-made mimics of biological receptors or enzymes that possess sites for molecular recognition and catalysis. Molecular imprinting involves creating template-shaped cavities in polymer matrices with the memory of the template molecules used for molecular recognition. This system is based on the "lock and key" model which is the system used by enzymes for substrate recognition. Enzymes have active binding sites with a unique geometric structure which selectively bind to a substrate having a corresponding shape.

In prior art molecular imprinting processes, substrate-selective recognition sites are prepared in a matrix using a casting procedure with a template molecule. Functional monomers attach to, or assemble around, a template molecule and the functional monomers and the template molecule are subsequently linked together by a cross-linking agent to form a molecularly imprinted polymer network. Removal of the template molecule from the molecularly imprinted polymer network creates a structure complementary to the template structure allowing its tight and selective uptake.

Despite the broad use of the above described molecular imprinting technique, there are inherent limitations with this process that decrease its practical suitability for sensors and other applications such as use in bioanalytical assays. For example, one inherent limitation is the inability for polymers to generate molecule size cavities with structure details due to the non-structure orientation around the templates and the macro-scale nature of the prior art molecular imprinting process. It is difficult to use a polymer as a building matrix to make molecule size recognition hosts. Another limitation is that the molecular recognition for sensor application is separated from transduction. For example, in nature, where there are ion channels in membranes, it is hard to distinguish molecular recognition from transduction, the two main components of sensors, as they are integrated and not separable. Other limitations and problems with the prior art molecular imprinting technique described above include heterogeneity in binding affinities, slow mass transfer in and out of the polymer matrix or network, overall low binding affinity, lack of a read-out for complexation, and slow template leaching.

Accordingly, there is a need for sensors and a method for producing sensors that overcomes these limitations and problems. In particular there is a need for sensors with enhanced selectivity, sensibility, and stability that provide molecular recognition cavities with antibody-like ability to bind and discriminate between molecules or other structures, and methods for making the same. The discovery of a nano-tunneling effect in sensors made in accordance with the present invention will open a new view point to current science. The application of a nano-tunneling effect in sensors made in accordance with the present invention can be used to build next generation biosensors and can also be used in other analytical assay applications.

SUMMARY OF THE INVENTION

In accordance with various aspects of the present invention, universal molecular sensors are provided as well as universal molecular sensors having a nano-tunneling effect which provides new and unique properties. Methods for making the sensors and realizing the nano-tunneling effect are also provided. In accordance with one exemplary embodiment, the sensor of the present invention is produced by a process of providing one or more molecules for use as molecular building blocks, providing a transducer having a surface capable of interacting with the molecular building blocks, providing one or more template molecules which may include providing more than one kind of template molecule, providing one or more solvents to create a solvent solution, adding the molecular building blocks, the template molecules, and the transducer to the solvent solution to create a matrix, removing the matrix from the solvent solution which has since become a deposition solution, and rinsing the matrix on the transducer with one or more solvents or other solutions to extract the template molecules thereby resulting in an imprinted sensor for the template molecules. The molecularly imprinted sensor has one or more molecular recognition cavities formed on the surface of the transducer and the molecular recognition cavities may be nanoscale molecular recognition cavities depending on the size of the templates used.

In one aspect of the present invention, the molecular building blocks may include monomers, molecules, ions, polyatomic ions, salts, complexes, or other compounds, pure chemical elements, elemental molecules, and/or crystals. In another aspect of the present invention the transducer may include polymers, optical fibers, metals, semiconductors, glasses, plastics, organic materials, and/or inorganic materials. In addition, the transducer substrate may take the form of any shape and may include any size of material from bulk size materials to nanometer size materials or nanostructures, such as carbon nanotubes, nanowires, nanoparticles, nanorodes etc. Moreover, the transducer may be comprised of nanoscale materials that undergo a nano-tunneling effect with the molecular recognition cavities imprinted on it or with other molecules or materials on the nanoscale transducer, thereby resulting in a sensor that possesses additional and/or new properties not previously found in either the substrate imprinted molecular recognition cavities or other molecules or materials on a bulk material based transducer, or the nanoscale transducer itself.

In still another aspect of the present invention, the template molecule or molecules may include small molecules, biological macromolecules, microorganisms, crystals, viruses, and/or any other material needing sensing, detection, separation, extraction, identification, adsorption, capturing or any other functional process. In still another aspect of the present invention, the interaction between the surface of a transducer and the molecular building blocks may include covalent bonding, non-covalent bonding, hydrophobic forces, van der Waals forces, pi-pi interactions, ionic interactions, electrostatic forces, and/or other interactions that keep the template molecule or molecules within the matrix formed within the deposition solution.

In another exemplary embodiment of the present invention, the resulting molecular recognition substrate imprinted sensor may be cured.

The present invention also includes a method for making a sensor which includes the steps of a) providing one or more molecules for use as molecular building blocks and a transducer having a surface capable of interacting with the molecular building blocks, b) providing one or more template molecules which may include providing more than one kind of template molecule, c) adding the molecular building blocks and the template molecules to one or more solvents to create a deposition solution, d) adding the transducer to the deposition solution to create a matrix via the interaction between the building blocks and the surface of the transducer, e) removing the transducer containing the matrix from the deposition solution, and f) rinsing the transducer containing the matrix with one or more solvents or other solutions to extract the template molecules and expose an imprinted sensor. In one exemplary embodiment of the present invention, the method for making a sensor may further include the step of synthesizing the molecular building blocks to have a specific function to interact with the surface of the transducer. In another exemplary embodiment of the present invention, the method for making a sensor may further include the step of pre-modifying or pre-treating the surface of the transducer with one or more specific functional groups that interact with the molecular building blocks. In yet another exemplary embodiment of the present invention, the method for making a sensor may further include the step of carrying out a post-synthetic functionalization process to increase the affinity and/or selectivity of the imprinted sensor.

Another exemplary embodiment of the method for making a sensor of the present invention includes the steps of a) providing one or more molecules for use as molecular building blocks, a transducer having a surface capable of interacting with the molecular building blocks, and one or more template molecules which may include providing one or more kinds of template molecules, b) providing one or more solvents to create a solvent solution, c) adding the molecular building blocks, the transducer, and the template molecule(s), in any order, to the solvent solution to create a matrix via the interaction between the molecular building blocks and the surface of the transducer, d) removing the transducer containing the matrix from the solvent solution which has since become a deposition solution, and e) rinsing the transducer containing the matrix with one or more solvents or other solutions to extract the template molecules and expose an imprinted sensor.

In addition, the methods of the present invention for making a sensor may include all of the aspects previously described above with respect to the sensor itself and the various components of the sensor.

The present invention utilizes molecule size building blocks for substrate imprinting the sensor with specific structure orientation instead of using polymers without any structure orientation (as done in the prior art) and employs the interaction between the molecule size building blocks and the surface of transducers to control the building block molecule orientation to define recognition cavities. As a result, specific molecule size recognition cavities can be formed.

When the transducer is a nanoscale material or a naturally occurring nanoscale material, the molecule size recognition cavities on it will result in a nano-tunneling effect that provides the molecular substrate imprinted sensor with new properties that are not already exhibited by either the molecule recognition matrix on a bulk material based transducer or the nanotransducer substrate itself. For example, molecular substrate imprinted potentiometric sensors could be used to detect any form of compounds, i.e. not just ions but also molecules, with enhanced selectivity, sensitivity, and stability.

Further aspects of the invention and areas of applicability will become apparent from the description provided herein. It should be understood that the description and specific examples are intended for purposes of illustration only and are not intended to limit the scope of the present invention.

BRIEF DESCRIPTION OF THE DRAWINGS

The drawings described herein are for illustration purposes only and are not intended to limit the scope of the present disclosure in any way. The present invention will become more fully understood from the detailed description and the accompanying drawings wherein.

DETAILED DESCRIPTION

Figure 1:
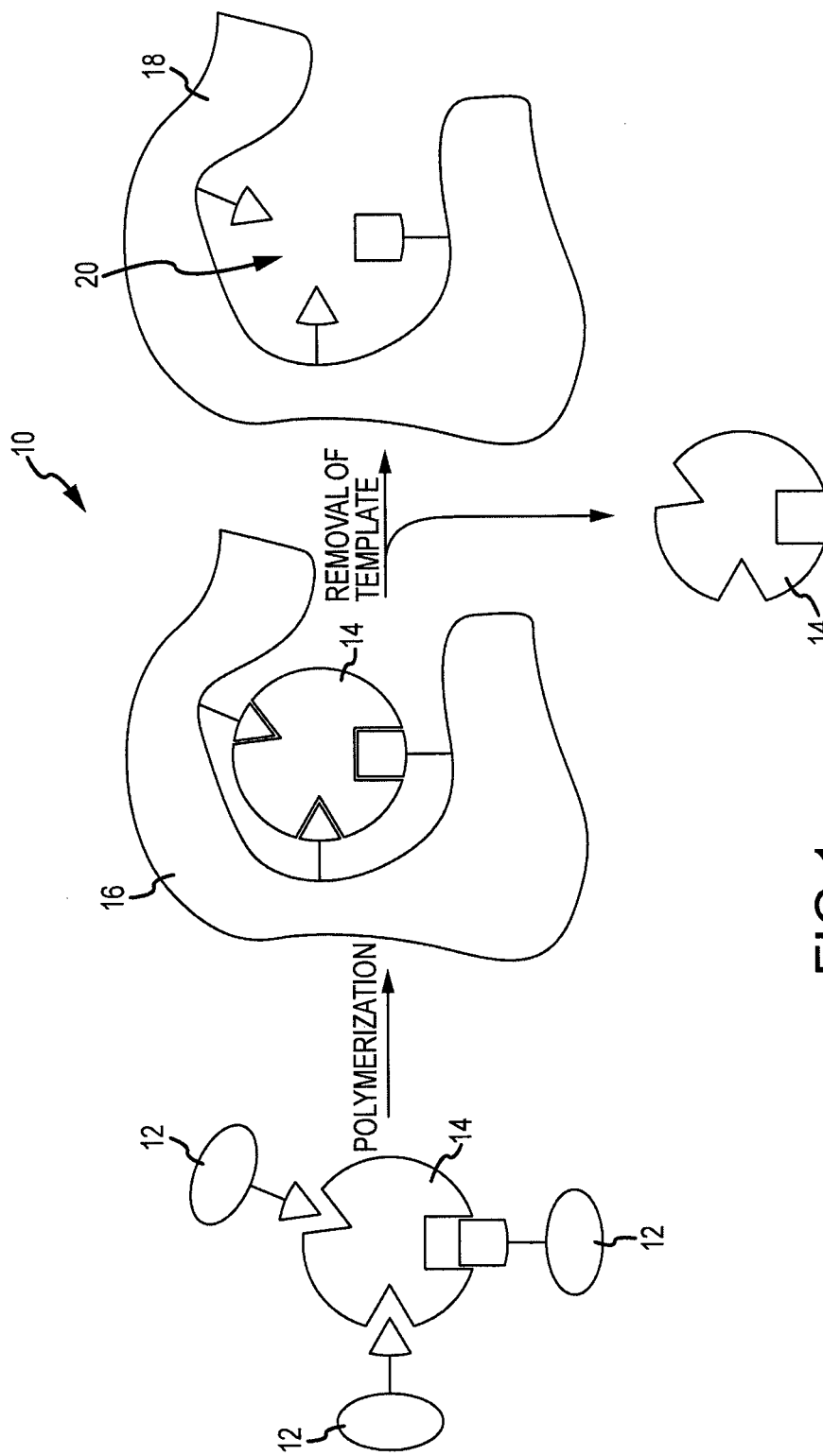
FIG. 1 is a diagram showing a prior art molecular imprinting technique.

The following description is merely exemplary in nature and is not intended to limit the present invention or its teachings, applications, or uses thereof. It should be understood that throughout the drawings, corresponding reference numerals indicate like or corresponding parts and features. The description of specific examples indicated in various embodiments and aspects of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features.

The present invention may be described herein in terms of various functional components and processing steps. It should be appreciated that such components and steps may be realized by any number of molecular components configured to perform the specified functions. For example, the present invention may employ molecular building blocks such as monomers, molecules, ions, salts, complexes, or other compounds, pure chemical elements, elemental molecules, crystals, and other types of building blocks to interact with the surface of a transducer substrate in the presence of a template molecule(s) to create a matrix.

FIG. 1 is a diagram showing a prior art molecular imprinting technique. The prior art molecular imprinting technique 10 includes functional monomers 12 which are self-assembled around a template molecule 14 by interaction between function groups on both the template molecule and monomers. The functional monomers 12 are then polymerized to form an imprinted matrix 16. The template molecule 14 is then removed from the polymer matrix 16 to leave behind an imprinted material 18 having a cavity 20 complementary in size and shape to the template 14. The cavity 20 works as a selective binding site for a specific template molecule. The prior art molecular imprinting technique utilizes covalent bonding or non-covalent bonding between the monomer and template to build the specific binding sites within the polymers. The present invention differs from the prior art molecular imprinting technique in that the present invention does not require bonding between the molecular building blocks and the templates. Instead the present invention focuses on the bonding or interaction of the molecular building blocks with the surface of transducer substrates. The sensor of the present invention is generated during the self-assembling or other process of the molecular building blocks to the surface around the templates. This mimics the biological machinery and offers a great level of control over the structure of materials compared to the three-dimensional matrix due to high orientation of the structure, and allows this molecular substrate imprinting system to build template molecule structures in more detail.

The present invention uses the molecular interaction between molecules (used as building blocks for the sensor) and a surface to generate molecular recognition pin holes on the surface. Unlike prior art molecular imprinting techniques, there is no specific bonding required between the monomers or molecules that act as building blocks and the template molecules. Instead, the present invention employs the interaction between the molecular building blocks and the surface of a transducer substrate to develop the specific molecular recognition cavities for sensing purposes. Thus, this molecular substrate imprinting technique of the present invention is not a covalent imprinting or a non-covalent imprinting, but is instead an imprinting approach that does not require bonding or interaction between the template molecules and the monomers or molecular building blocks. In particular, the molecules will self-assemble, polymerize, polymerize after self-assembling, electro-polymerize, or use other reactions to interact with the surface of transducers in the presence of templates, such as small molecules, biological macromolecules, microorganisms, whole crystals, viruses, and/or any other material needing sensing, detection, separation, extraction, identification, adsorption, capturing, or other any other functional process. Because there is no interaction between the templates and the surface of the transducer during the molecular substrate imprinting process, the templates are only physically trapped within the matrix on the surface of the transducer and can be easily washed away. Removal of the templates from the matrix generates a structure complementary to the template structure or to an analogous structure on the surface of the transducer substrate and results in a substrate imprinted sensor.

The present invention enables the creation of universal molecular recognition cavities in sensors because the interaction to build the recognition cavities is between the molecule and the surface of sensors' transducers, not between the molecules/monomers and templates. The present invention ensures that the building molecules assembled around the templates are oriented with a great level of control over the material's structure. The sensor resulting from the present invention still provides three dimensional recognition cavities but with one dimension as the transducer that is an open bottom with thin film cavities on it that will act as a filter to allow molecules with the same geometrical features of the displaced molecules to enter. This property assures the assessability for the subsequent sensing process. Accordingly, it can be subsequently used to detect molecular details in a more precise manner. Only the smallest building block molecules with specific orientation are able to form a matrix around the template molecules and copy their specific structure with detail.

Figure 2:
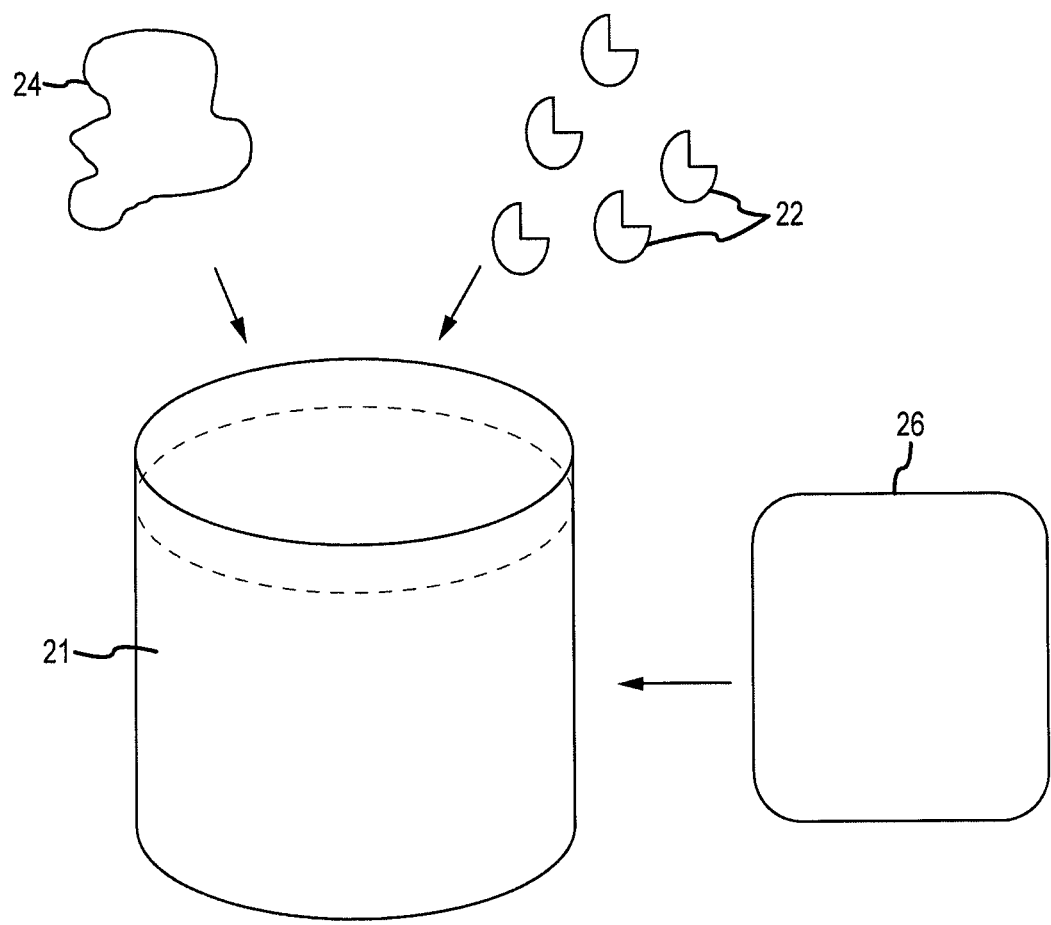
FIG. 2 is an illustration showing the components that are combined to create the sensor of the present invention.
Figure 3:
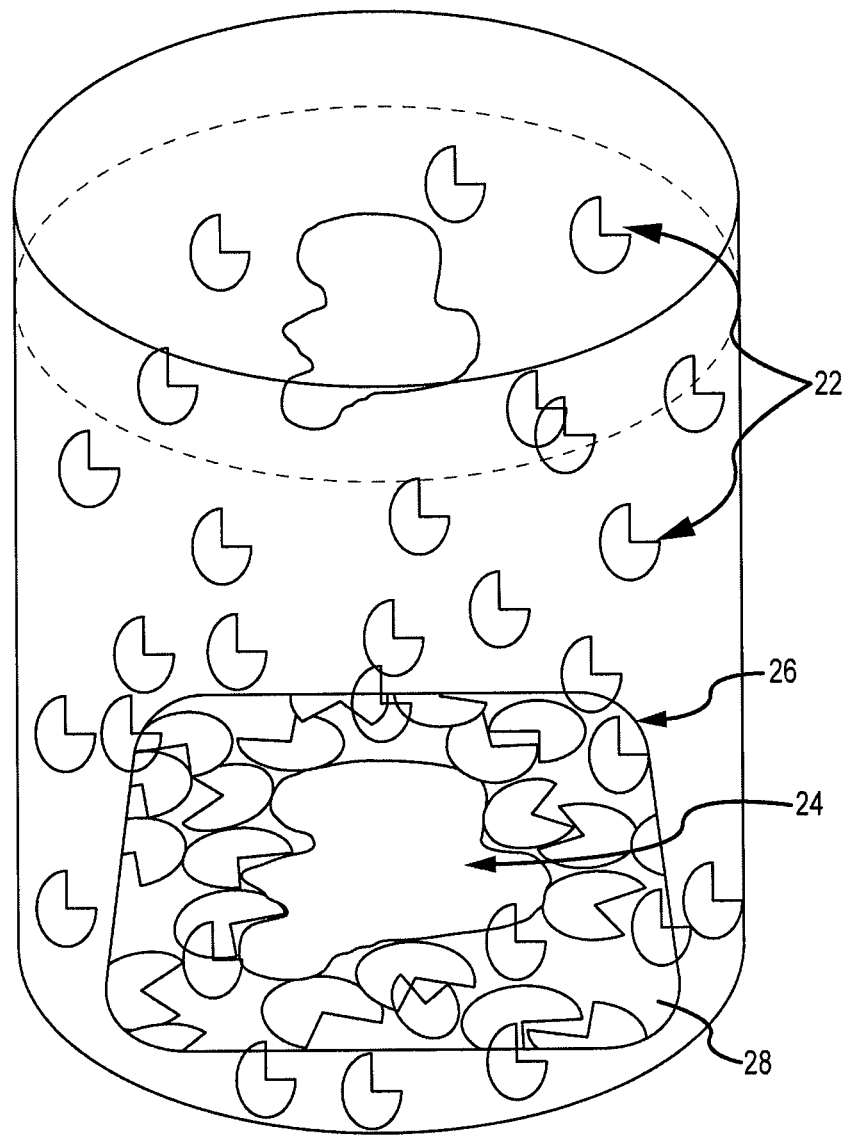
FIG. 3 is an illustration showing a sensor created by the interaction between the molecular building blocks and the surface of a transducer substrate in the presence of a template molecule.

FIG. 2 is an illustration showing the components that are combined to create the sensor of the present invention. One or more solvents are combined to create a solvent solution 21. Molecular building blocks 22, one or more template molecules 24, and a transducer substrate 26 having a surface capable of interacting with the molecular building blocks 22 are all added to the solvent solution 21. The molecular building blocks 22, the template molecule(s) 24, and the transducer substrate 26 can be added to the solvent solution 21 in any sequence depending upon the imprinting system. FIG. 3 is an illustration showing a sensor 28 created by the interaction between the molecular building blocks 22 and the surface of the transducer substrate 26 in the presence of the template molecule 24.

The molecules used for the molecular building blocks are carefully selected to interact with the surface of transducer substrates to form a recognition matrix. The molecules should have functional groups that could react with the surface of transducer substrates, or form a film on the surface of transducer substrates, by self-assembling, polymerizing, polymerizing after self-assembling, or carrying out other reactions to interact with the surface of the transducer substrate. The molecular building blocks may include monomers, molecules, ions, polyatomic ions, salts, complexes, or other compounds, pure chemical elements, elemental molecules, crystals, or any other component that will interact with the surface of a transducer substrate to form a sensor. The interaction between the molecular building blocks and the surface of the transducer substrate may include covalent bonding, non-covalent bonding, hydrophobic forces, van der Waals forces, pi-pi interactions, ionic interactions, electrostatic interactions, and/or other interactions that keep the template molecule or molecules within the matrix formed within the deposition solution. The transducer substrate may be a solid material that may include polymers, optical fibers, metals, semi-conductors, glasses, plastics, organic materials, inorganic materials, and/or the like. The transducer substrate may take the form of any shape such as planar, round, curved surfaces, etc. and may comprise any size of material from bulk size materials to nanometer size materials or nanoscale nature materials, such as indium-tin oxide.

The solvent or solvents used to make the deposition solution must enable the molecular building blocks to interact with the surface of the transducer substrate to form specific recognition cavities on the surface of the transducer substrate in the presence of template molecules. The molecular building blocks should be soluble in the solvent or solvents. The template molecule could be soluble or insoluble in the deposition solution. The template molecule or molecules may include small molecules, biological macromolecules, microorganisms, crystals, viruses, and/or any other material needing sensing, detection, separation, extraction, identification, adsorption, capturing, or any other functional process.

Figure 4:
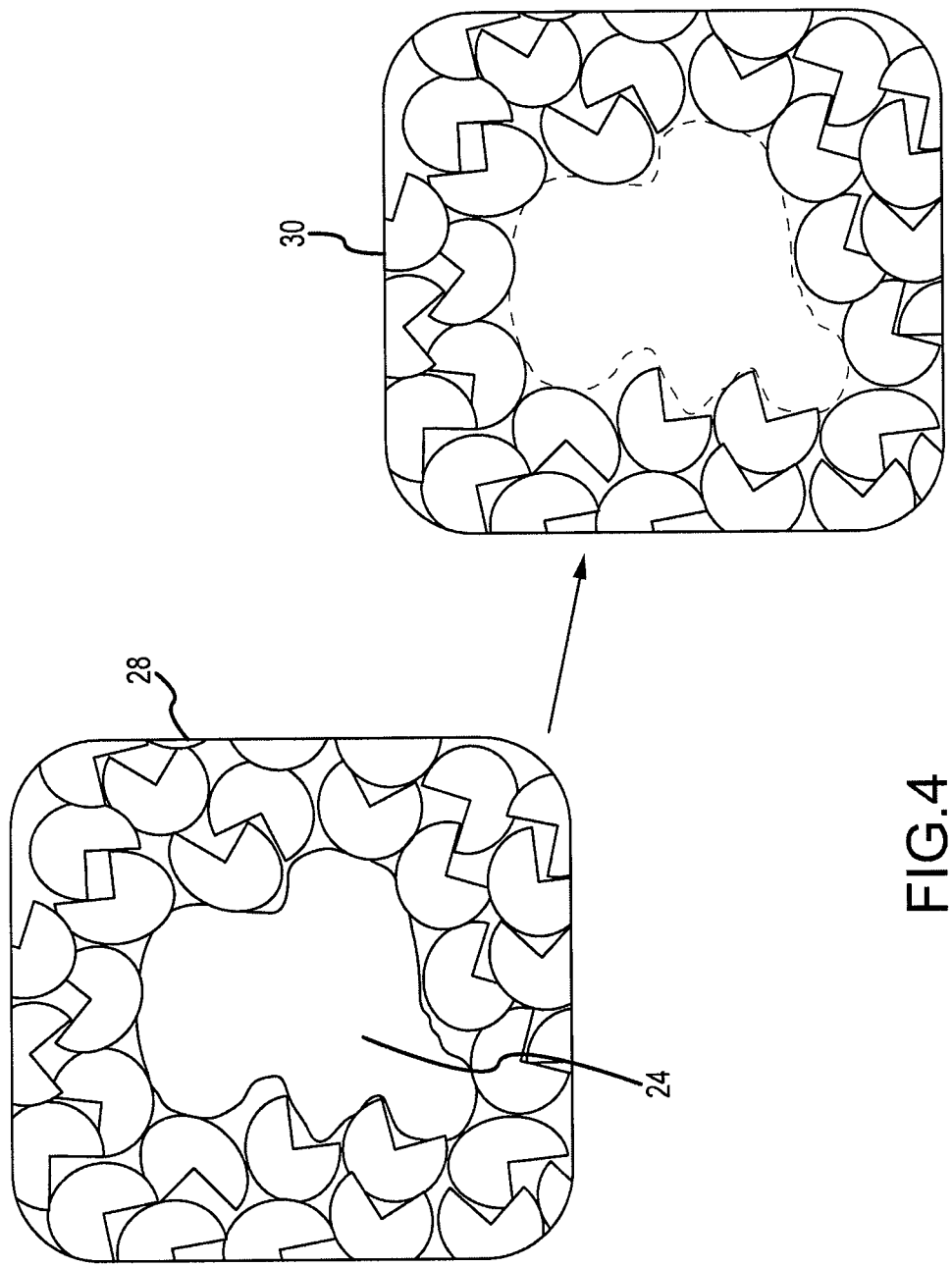
FIG. 4 is an illustration showing the rinsing of the matrix to remove the template molecule in order to create an imprinted transducer substrate capable of functioning as a sensor for the template molecule.

FIG. 4 is an illustration showing the rinsing of the matrix 28 to remove the template molecule 24 in order to create a molecular imprinted sensor. The matrix 28 is rinsed with one or more solvents or other solutions that are able to extract the template molecules from the matrix. All of the template molecules should be easily extracted out of the matrix.

With the present invention, there is no bonding required between the molecular building blocks and the templates so there is no need to carefully design the interactions. Accordingly, the present invention simplifies the sensors' imprinting process and allows the templates to be removed easily and completely. The sensor of the present invention results in biological host like cavities that will bind to particular molecular structures strongly and specifically. In addition, the sensor generated by the present invention is two-dimensional with the other dimension being the surface of the transducer. Therefore, it will produce easy readout as soon as the molecules are able to enter the cavities. No coating process is needed since the recognition cavities are already built on the surface of the transducer. The molecular recognition matrix of the present invention simplifies the sensor fabrication process and makes the transition of binding into an easy readout. Since the matrix is on the surface of transducers and the building block molecules are bonded to the surface, the thickness of the sensing film is controllable and can be very thin, sometimes as thin as a monolayer. This very thin film can be clearly produced and reproduced making it particularly applicable for the development of optical and acoustic sensors.

Figure 5:
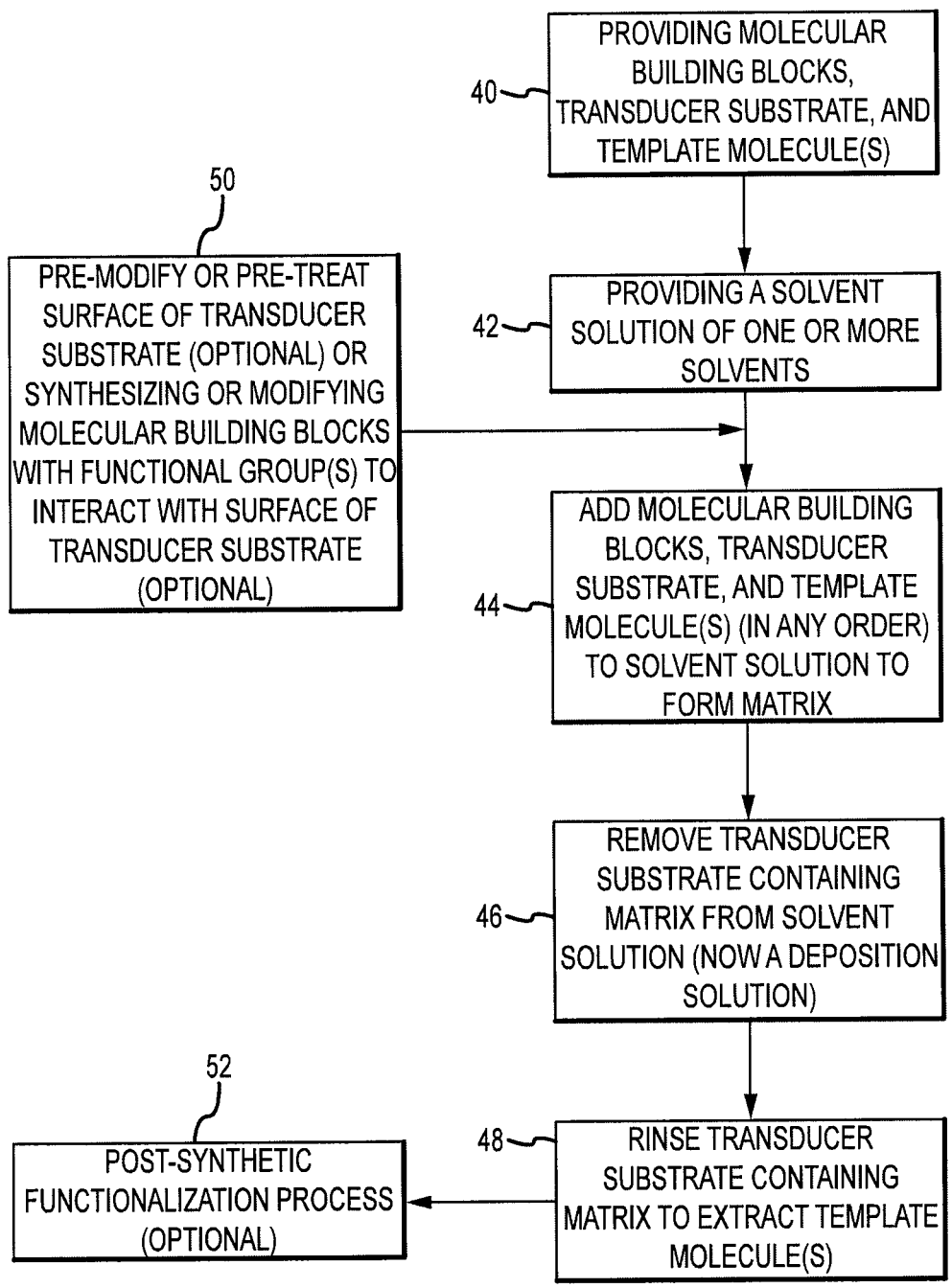
FIG. 5 is a flowchart showing an exemplary method of the present invention for making the sensor.

FIG. 5 is a flowchart showing an exemplary method of the present invention for making a sensor. First, in step 40, molecular building blocks, a transducer substrate, and one or more template molecules, which may include one or more kinds of template molecules, are provided. Next, a solvent solution of one or more solvents is provided in step 42 and the molecular building blocks, transducer substrate, and template molecule(s) are added to the solution in step 44 to form a matrix. The molecular building blocks, transducer substrate, and template molecule(s) can be added to the solvent solution in any order or sequence depending on the purpose or type of imprinting system. Next, in step 46, the transducer substrate containing the matrix is removed from the solvent solution which has since become a deposition solution. Finally, the transducer substrate containing the matrix is rinsed in step 48 to extract the template molecule(s).

The method for making the sensor of the present invention shown in FIG. 5 may also further include the step of pre-modifying or pre-treating the transducer surface or the surface of a substrate with a nanoscale transducer on it with one or more specific functional groups that interact with the molecular building blocks (step 50), or synthesize or modify the molecular building blocks with one or more specific functional groups that interact with the surface of transducers. In addition, the method shown in FIG. 5 may also further include the step of carrying out post-synthetic functionalization process to increase the affinity and/or selectivity of the imprinted sensor (step 52).

In one exemplary application of the present invention, a sensor can be fabricated that has enhanced binding abilities with high selectivity to discriminate between molecules and other structures. For example, the method for making a sensor of the present invention can be used to make an acetic acid sensor.

The materials used to make the acetic acid sensor included octadecyltrichlorosilane (OTS) as the molecular building blocks, acetic acid as the template molecule, indium-tin oxide (ITO) coated glass as the transducer substrate, and $CHCl_3/CCl_4$ as the solvent solution. The ITO substrate was pre-treated to have hydroxyl groups. Acetic acid ([acetic acid] $=3.0\times10^{-2}$ M) and OTS ([OTS]$=1.33\times10^{-3}$ M) were co-adsorbed on the surface of the ITO glass plate from the $CH_3/CH_4$ solution (2:3 v/v) at 0° C. for three minutes. The ITO electrode substrate was rinsed with $CHCl_3$ (30×1 ml) to remove the embedded acetic acid molecules and followed by drying at room temperature for 12 hours.

Figure 6:
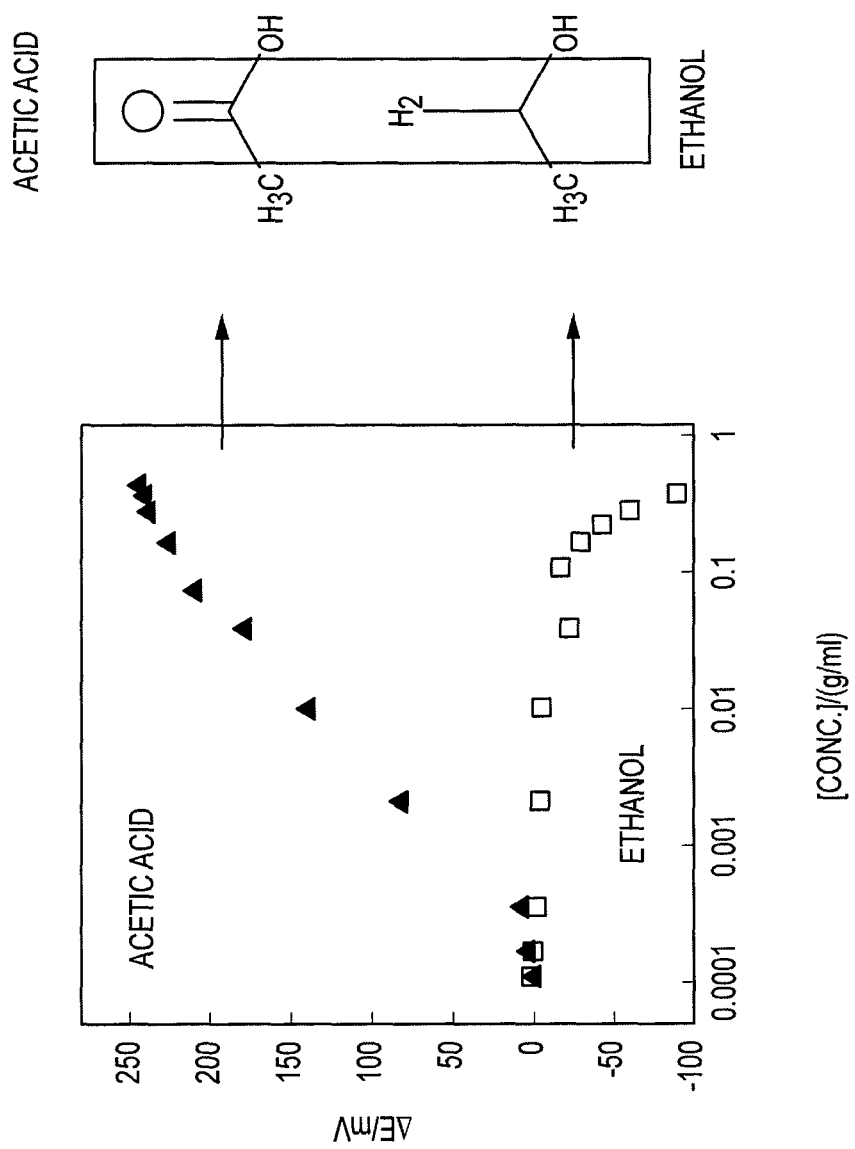
FIG. 6 is a graph showing the potentiometric responses of an acetic acid sensor to acetic acid and ethanol.

FIG. 6 is a graph showing the potentiometric responses of the acetic acid substrate imprinted sensor for both acetic acid and ethanol, a compound having a structure similar to acetic acid. In measuring the potentiometric response, a two-electrode system was used consisting of an Ag/AgCl (saturated KCl) reference electrode and the acetic acid sensor made in accordance with the present invention as the working electrode. The potentials of the sensor were measured against the Ag/AgCl reference electrode with an Orion 920A potentiometer. As can be seen in FIG. 6, the acetic acid sensor displayed very specific molecular recognition ability and gave high responses towards acetic acid (FIG. 6 curve (▲)). Acetic acid selectively bound to the octadecylsiloxane (ODS) layer film compared to ethanol molecules (FIG. 6, curve (□)), which have a structure similar to the acetic acid molecules. Ethanol did not produce any false positive response in acetic acid recognition cavities. This confirms that acetic acid was initially incorporated into the molecular substrate imprinted film and extracted away to create the molecular recognition cavities. Since there is no bonding required between the molecular building blocks and target (templates) molecules, this molecular substrate imprinting technique can be used to develop universal sensors. ITO is known as a degenerate n-type semiconducting material possessing structural features with vertical column growth in multiple orientations. The individual columns are single crystals, and the grain size ranges from a few nanometers to a few tens of nanometers. This acetic acid nanosensor demonstrated a 75.6 mV/decade sensitivity to protons of monovalent acetic acid and depicted high sensitivity for monovalent cation, where the sensitivity/slope of the Nernst plot for bulk material based electrodes should be 59.1 mV/decade. This graph exemplifies the enhanced sensitivity and selectivity of the acetic acid sensor made in accordance with the present invention, as well as long term stability since the covalent bonding between the OTS and ITO substrate is used to build the acetic acid molecular recognition matrix with no biological recognition elements involved.

In another exemplary application of the present invention, a chloramphenicol sensor is made in accordance with the method of the present invention. The materials used to make the chloramphenicol sensor included OTS as the molecular building blocks, chloramphenicol as the template molecule, ITO coated glass as the transducer substrate, and $CHCl_3/CCl_4$ as the solvent solution. As with the molecular substrate imprinting procedure used for developing the acetic acid sensor, OTS ([OTS]=$1.36\times10^{-3}$ M) and chloramphenicol ([chloramphenicol]=$1.5\times10^{-2}$ M) were co-deposited on the surface of an ITO glass plate in the presence of the $CH_3/CH_4$ solution (2:3 v/v) at 0° C. for four minutes. The ITO transducer substrate was then rinsed with chloroform (30×1 ml) to remove the embedded chloramphenicol template molecules followed by drying at room temperature for 12 hours.

Figure 7:
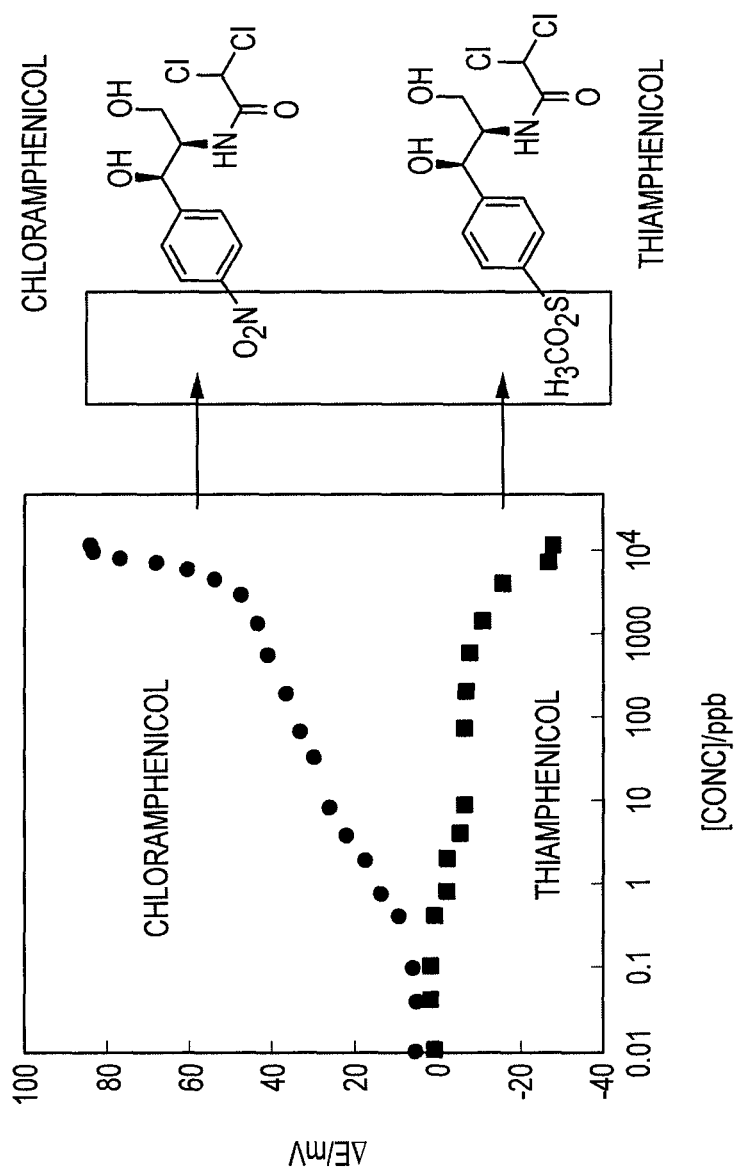
FIG. 7 is a graph showing the potentiometric responses of a chloramphenicol sensor to chloramphenicol and thiamphenicol.

With the chloramphenicol sensor made in accordance with the present invention, the integration of the specific molecule scale recognition cavities and the nanoscale transducers resulted in a nano-tunneling effect on the chloramphenicol sensor's performance. As shown in FIG. 7, the structure of chloramphenicol is not an ionic compound and does not have any charge group. Accordingly, it would not show any potential responses in solution with a potentiometer. In other words, the chloramphenicol imprinted sensor cannot be an ion selective electrode (ISE) or sensor. However, as can be seen in FIG. 7 curve (●), the chloramphenicol sensor demonstrated a potential change to chloramphenicol at zero current. The size of the chloramphenicol recognition cavities in the chloramphenicol sensor made in accordance with the present invention is in nanometer scale or smaller, as mentioned above. When these nanoscale molecular recognition cavities lay on the nanoscale substrate (the ITO transducer substrate used for the chloramphenicol sensor), the 'neutral' electrical charge chloramphenicol molecule demonstrates a fraction of ionic properties and produces a potentiometric response on a potentiometer (see FIG. 7, curve (●)). As a result, chloramphenicol molecules can be detected and recognized by a potentiometer or a volt meter.

A molecular recognition cavity should possess the exact shape and geometrical properties of the molecules that are used as template molecules. Since the film formed around the recognition cavities is done with a great level of control over material structure and orientation, it can be subsequently used to detect molecular details in a more precise manner. As can be seen in FIG. 7 curve (●), the chloramphenicol molecules were detected by the chloramphenicol sensor made in accordance with the present invention while the thiamphenicol molecules, which have a structure similar to the chloramphenicol molecules, did not generate any false positive potentiometric response on the chloramphenicol sensor (FIG. 7 curve (■)). Therefore, the chloramphenicol substrate imprinted sensor displayed very specific molecular recognition ability and gave high response to chloramphenicol. In addition to the new and additional properties of the chloramphenicol sensor, this graph exemplifies the increased sensitivity and selectivity of the chloramphenicol sensor made in accordance with the present invention. Integration of the molecular recognition matrix and nanotransducers generates a nano-tunneling effect, and this effect produces new properties that are not demonstrated by either the molecular recognition matrix or the nanotransducers. A neutral electrical charge molecule demonstrates a fraction of ionic properties and can be detected by potentiometry. In other words, the molecularly substrate imprinted potentiometric sensing system of the present invention is a universal sensor system that can be used to recognize any compounds regardless of their properties.

The operation range and limit of detection (LOD) of nano-tunneling sensors may be pushed down several orders of magnitude lower than expected. As shown in FIG. 7 curve (●), the operation concentration range of the sensor for chloramphenicol varied from $3.0\times10^{-10}$ to $3.6\times10^{-5}$ M, while the calibration range for potentiometry is supposed to be $1\times10^{-7}$ to $1\times10^{-1}$ M. In short, building molecular recognition cavities on the surface of nanotransducers will cause a nano-tunneling effect. This nano-tunneling effect enables one to build universal sensors including sensors having new properties not previously exhibited by the separate components used to create the sensors.

In addition, a nano-tunneling effect that takes place between the molecular recognition cavities and the surface of the nanoscale substrate provides a sensor with new properties that neither the molecular recognition matrix, nor the nanotransducer would generate by themselves. For example, a bare carbon nanotube (CNT) based field effect transistor generates about 0.3 µA for saturated ethanol vapor. When coating ethanol recognition cavities directly on the surface of CNTs by this molecular substrate imprinting technique, the resulting sensor only needs about 0.80 mmHg to produce the same amount of current, namely 0.3 µA. The sensitivity of the nano-tunneling effect based sensor is about 950 times higher than that of the CNT nanoscale transducer itself, not to mention that about 70% of the CNT surface was covered with a molecular recognition matrix.

Furthermore, when molecules or macromolecules, such as biomolecules or polymers, are in the nanometer scale range, a nano-tunneling effect will be generated when molecules or macromolecules are integrated with the nanoscale substrates thereby producing some new properties that may be used for analytical or bioanalytical application. For example, electroinactive compounds can generate electro-active properties and display redox peaks at cyclic voltametry (CV), and non-optical compounds can show optical properties, or other new properties that were not previously demonstrated on bulk materials even with the same composition.

It has demonstrated that the present invention can be used to develop universal sensors. The present invention can also be used to make solid-state extraction (SPE) adsorbents, that can be applied in separation, pre-concentration, adsorption, or other analytical or bioanalytical assay applications. The nano-tunneling effect exhibited by the sensors made in accordance with the present invention provides a different way to make chemical and biological sensors. The two basic components of the sensor, namely the transducer and the selective layer, need to both be in nanoscale range or lower and integrated. The nano-tunneling effect will appear only if these requirements are satisfied. One way to realize this is to use the molecular substrate imprinting technique of the present invention to coat the selective layer with molecular recognition cavities possessing antibody-like ability on the nanoscale transducers.

The present invention has been described above with reference to various exemplary embodiments. However, those skilled in the art will recognize that changes and modifications may be made to the exemplary embodiments without departing from the scope of the present invention. For example, the various steps, as well as the components for carrying out the steps, may be implemented in alternate ways depending upon a particular application. These and other changes or modifications are intended to be included within the scope of the present invention, as set forth in the following claims.

The invention claimed is:

1. A chloramphenicol sensor having the ability to detect molecules or other structures that is produced by a process of providing one or more molecules for use as molecular building blocks, providing a transducer substrate having a surface capable of interacting with the molecular building blocks, providing one or more chloramphenicol template molecules which may include providing more than one kind of template molecule, providing one or more solvents to create a solvent solution, adding the molecular building blocks, the chloramphenicol template molecules and the transducer substrate to the solvent solution to create a matrix on the transducer substrate, removing the transducer substrate containing the matrix from the solution, and rinsing the matrix with another of at least one solvent or solution to extract the chloramphenicol template molecules thereby resulting in a substrate imprinted chloramphenicol sensor having molecular recognition cavities for the chloramphenicol template molecules wherein the substrate imprinted chloramphenicol sensor possesses additional properties that are not present in the molecular recognition cavities or the transducer substrate.

2. The sensor of claim 1 wherein nano-tunneling takes place between the molecular recognition cavities and the surface of the transducer substrate which comprises a nanoscale transducer.

3. The sensor of claim 1 wherein the molecular building blocks comprise at least one of a monomer, a molecule, an ion, a polyatomic ion, a salt, a complex, a compound, a pure chemical element, an elemental molecule, and a crystal.

4. The sensor of claim 1 wherein the transducer substrate comprises a solid material comprising at least one of a polymer, an optical fiber, a metal, a semiconductor, a glass, a plastic, an organic material, and an inorganic material.

5. The sensor of claim 1 wherein the transducer substrate may comprise any shape.

6. The sensor of claim 1 wherein the transducer substrate may comprise any size of material from bulk size materials to nanometer size materials or structures.

7. The sensor of claim 1 wherein the transducer substrate is a nanotransducer and nano-tunneling takes place within molecules or materials on the nanotransducer.

8. The sensor of claim 1 wherein the transducer substrate is a nanoscale transducer substrate and the molecular recognition cavities are nanoscale size or less molecular recognition cavities.

9. The sensor of claim 4 wherein the transducer substrate comprises an indium-tin oxide coated glass.

* * * * *